United States Patent [19]

Matsuda et al.

[11] Patent Number: 5,166,453

[45] Date of Patent: Nov. 24, 1992

[54] METHOD FOR PURIFICATION OF ETHYLENE COMPOUNDS HAVING FLUORINE-CONTAINING ORGANIC GROUP

[75] Inventors: Takashi Matsuda; Hirofumi Kishita; Shinichi Sato, all of Annaka; Koichi Yamaguchi, Takasaki; Kouji Takano, Annaka; Shuji Suganuma, Takasaki, all of Japan

[73] Assignee: Shin-Etsu Chemical Co., Ltd., Tokyo, Japan

[21] Appl. No.: 725,526

[22] Filed: Jul. 3, 1991

[30] Foreign Application Priority Data

Jul. 5, 1990 [JP] Japan ................................ 2-178216

[51] Int. Cl.$^5$ .................... C07C 41/34; C07C 17/38
[52] U.S. Cl. .................................. 568/621; 568/615; 568/674; 568/677; 568/682; 568/699; 570/158; 570/177; 570/171; 570/180

[58] Field of Search ............... 568/682, 615, 621, 674, 568/677, 699; 570/158, 177, 180, 171

[56] References Cited

U.S. PATENT DOCUMENTS

| | | | |
|---|---|---|---|
| 3,046,261 | 7/1962 | Iserson | 570/171 |
| 3,053,815 | 9/1962 | Barr | 570/158 |
| 3,317,618 | 5/1967 | Haszeldine | 562/101 |
| 4,275,226 | 6/1981 | Yamabe et al. | 568/674 |

*Primary Examiner*—Howard T. Mars
*Attorney, Agent, or Firm*—Oblon, Spivak, McClelland, Maier & Neustadt

[57] ABSTRACT

A purification method of a fluorine-containing alkylethylene comprises reacting the fluorine-containing alkylethylene with powdered metallic zinc in the presence of an aqueous acetic acid solution. By this method, fluorine-containing alkyl iodide and fluorine-containing alkylethyl iodide, contained as impurities in the fluorine-containing alkylethylene, can be removed effectively, for example, to a level of 1 ppm or below.

7 Claims, No Drawings

METHOD FOR PURIFICATION OF ETHYLENE COMPOUNDS HAVING FLUORINE-CONTAINING ORGANIC GROUP

BACKGROUND OF THE INVENTION

1. Field of the Invention

This invention relates to a method for purification of ethylene compounds having a fluorine-containing organic group, typically a fluorine-containing alkylethylene, and more particularly to a method for removal of impurity iodine compounds from a fluorine-containing alkylethylene.

2. Description of the Prior Art

Fluorine-containing alkylethylenes generally perform an addition reaction with a hydrosilane or a hydrosiloxane extremely rapidly, to give addition reaction products in high yields, and are therefore very important compounds for silicon chemistry.

Such fluorine-containing alkylethylenes are prepared by reacting a fluorine-containing alkyl iodide with ethylene to form a fluorine-containing alkylethyl iodide and reacting the thus formed alkylethyl iodide with an alkali, e.g. potassium hydroxide, as represented by the following reaction formula:

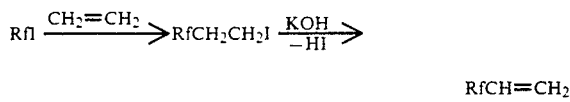

$$RfI \xrightarrow{CH_2=CH_2} RfCH_2CH_2I \xrightarrow[-HI]{KOH} RfCH=CH_2$$

wherein Rf is a fluorine-containing organic group.

However, the fluorine-containing alkylethylene obtained in this manner contains traces of the fluorine-containing alkyl iodide, used as the starting material, and the intermediate, fluorine-containing alkylethyl iodide. Where the fluorine-containing alkylethylene thus prepared is used as such for an addition reaction with a hydrosilane or hydrosiloxane, therefore, the fluorine-containing alkyl iodide or alkylethyl iodide act as a catalyst poison, thereby lowering the yield of the desired addition reaction product.

SUMMARY OF THE INVENTION

It is accordingly an object of this invention to provide a method by which fluorine-containing alkyl iodides and/or fluorine-containing alkylethyl iodides contained as impurities in an ethylene compound having a fluorine-containing organic group, such as a fluorine-containing alkylethylene, can be removed easily from the ethylene compound.

A method for purification of an ethylene compound having a fluorine-containing organic group, according to this invention, comprises reacting the ethylene compound having a fluorine-containing organic group with powdered metallic zinc in the presence of an aqueous acetic acid solution.

According to the method of this invention, iodine compounds contained as impurities in the ethylene compound are decomposed as expressed by the following formulas:

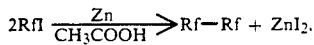

$$2RfI \xrightarrow[CH_3COOH]{Zn} Rf-Rf + ZnI_2.$$

$$2RfCH_2CH_2I \xrightarrow[CH_3COOH]{Zn} RfCH_2CH_2CH_2CH_2Rf + ZnI_2$$

wherein Rf is as defined above. The resulting salt ($ZnI_2$) and excess powdered metallic zinc are filtered off. The filtrate thus obtained will separate into two layers because the ethylene compound having a fluorine-containing organic group is heavier. By separating the lower layer containing the compound, the impurity iodine compounds can be removed easily in the upper layer. The fluorine-containing compounds formed on decomposition of the iodine compounds would be left in the ethylene compound purified. Because the fluorine-containing compounds have no iodine atoms, however, the presence of traces of these compounds as impurities in the ethylene compound having a fluorine-containing organic group will not affect adversely the addition reaction of the ethylene compound, or the like.

The fluorine-containing alkylethylene or the like having undergone the purification treatment according to this invention is able to give products in high yields through addition reaction with dimethylchlorosilane or the like, which products have been obtainable only in low yields heretofore. The addition products thus obtained are extremely useful for such applications as silylating agent, silica treating agent, etc.

The purification method of this invention is also applicable to, for example, difunctional fluorine-containing alkylethylene compounds having two ethylene groups, and the like. The alkylethylene compounds thus purified are able to give products in high yields through addition reaction with dimethylchlorosilane, similarly to the above, and the resulting addition products are useful as a starting material for hybrid silicones having a fluorine-modified backbone.

DETAILED DESCRIPTION OF THE INVENTION

The ethylene compound having a fluorine-containing organic group to be purified as the objective compound includes, for example, ethylene compounds which have a fluorine-containing organic group such as perfluoroalkyl groups, perfluoroalkyl ether groups, etc. More typical examples of the ethylene compound include perfloroalkylethylenes and ethylenes of which at least one hydrogen atom has been substituted by a perfluoroalkyl ether group. The application of the method of this invention is not limited to purification of monovalent ethylene compounds; namely, the method is also applicable to purification of difunctional ethylene compounds (i.e. compounds which have two ethylene groups) provided that the compounds contain iodine compounds, such as the aforementioned fluorine-containing alkyl iodides and fluorine-containing alkylethyl iodides, as impurities. More specifically, the method of this invention is applicable to purification of the following compounds:

$C_2F_5CH=CH_2$, $C_3F_7CH=CH_2$, $C_4F_9CH=CH_2$, $C_6F_{13}CH=CH_2$, $C_8F_{17}CH=CH_2$.

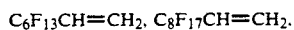
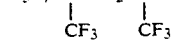
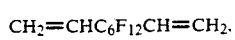

$$C_3F_7OCFCF_2OCFCH=CH_2.$$
$$\phantom{C_3F_7OCFC}|\phantom{F_2OC}|$$
$$\phantom{C_3F_7OC}CF_3\phantom{F_2O}CF_3$$

$CH_2=CHC_6F_{12}CH=CH_2.$

-continued

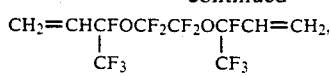

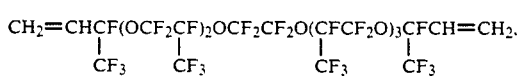

and

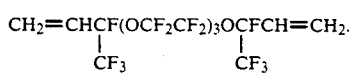

In the purification method according to this invention, the powdered metallic zinc is preferably used in an amount of from 20 to 5000 moles per mole of the iodine compound contained in the ethylene compound to be purified.

It is desirable that the aqueous acetic acid solution used in the method have an acetic acid concentration of from 0.5 to 99.0% by weight, particularly from 3.0 to 20.0% by weight. The aqueous solution of acetic acid is used preferably in an amount of from 0.5 to 3.0 moles, in terms of acetic acid, per mole of the metallic powdered metallic zinc.

The reaction, after the addition of the powdered metallic zinc and the aqueous acetic acid solution, may be carried out at a temperature of generally from 0° to 90° C., preferably from 20° to 50° C., for about 20 minutes to about 3 hours.

After the reaction is over, as described above, the resultant salts are removed by filtration and the filtrate is left to stand to allow it to separate into two layers. The lower layer is taken, to complete the purification treatment.

It is possible, by the above purification method, to lower the amount of impurity iodine compound in the ethylene compound to a level of 1 ppm or below.

EXAMPLES

Example 1

A 100 ml flask equipped with a reflux condenser and thermometer was charged with 40 g of perfluoro-n-butylethylene which contained 224 ppm of an iodine compound as impurities, 2 g of powdered metallic zinc and 35 g of a 5% aqueous solution of acetic acid, followed by stirring with a magnetic stirrer at room temperature for 30 minutes. The reaction mixture was then filtered, and the filtrate was allowed to separate into two layers and the lower layer was taken off.

The iodine content of the purified product thus obtained was determined, by potentiometric titration, to be below 1 ppm.

Comparative Example 1

The reaction, filtration of the reaction product, separation of the filtrate, and determination of iodine content were carried out in the same manner as in Example 1 except for not using the aqueous acetic acid solution. The iodine content of the purified product was 163 ppm.

Comparative Example 2

A reaction similar to that in Comparative Example 1 was carried out at 50° C., followed by filtration of the reaction product, separation of the filtrate, and determination of iodine content. The iodine content was found to be 95 ppm.

Example 2

The same flask as used in Example 1 was charged with 38 g of HFPO trimer-ethylene having the following formula:

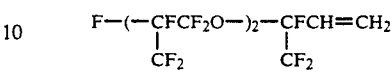

which contained 127 ppm of an iodine compound as impurities, 1.2 g of powdered metallic zinc and 29 g of a 10% aqueous solution of acetic acid, followed by stirring with the magnetic stirrer at room temperature for 1 hour. The reaction mixture was then filtered, and the filtrate was allowed to separate into two layers and the lower layer was taken off. Upon potentiometric titration, the iodine content of the purified product was found to be below 1 ppm.

Example 3

The same flask as used in Example 1 was charged with 35 g of a difunctional ethylene compound having the following formula:

which contained 753 ppm of an iodine compound as impurities, 6.3 g of powdered metallic zinc and 30 g of a 20% aqueous solution of acetic acid, followed by stirring with a magnetic stirrer at 40° C. for 2 hours. The reaction mixture was then filtered, and the filtrate was allowed to separate into two layers and the lower layer was taken off. Upon potentiometric titration, the iodine content of the purified product was found to be below 1 ppm.

Example 4

The same flask as used in Example 1 was charged with 44 g of a difunctional ethylene compound having the following formula:

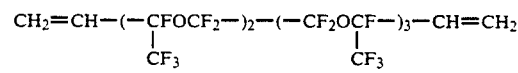

which contained 324 ppm of an iodine compound as impurities, 4.1 g of powdered metallic zinc and 45 g of a 10% aqueous solution of acetic acid, followed by stirring with the magnetic stirrer at room temperature for 3 hours.

The reaction mixture was then filtered, and the filtrate was allowed to separate into two layers and the lower layer was taken off. Upon potentiometric titration, the iodine content of the purified product was found to be below 1 ppm.

We claim:

1. A method of purification of an ethylene compound having a fluorine-containing organic group represented by the formula:

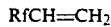

wherein Rf is a fluorine-containing organic group, containing an iodide compound as an impurity, which comprises the steps of:

bringing the ethylene compound into contact with powdered metallic zinc in the presence of an aqueous acetic acid solution, thereby the iodide compound reacting with the powdered metallic zinc, and separating the purified ethylene compound having a fluorine-containing organic group from the resulting reaction mixture.

2. The method according to claim 1, wherein the group Rf is a perfluoroalkyl group or a perfluoroalkyl ether group.

3. The method according to claim 1, wherein the ethylene compound having a fluorine-containing organic group comprises at least one compound selected from the group consisting of:

$C_2F_5CH=CH_2$, $C_3F_7CH=CH_2$, $C_4F_9CH=CH_2$, $C_6F_{13}CH=CH_2$, $C_8F_{17}CH=CH_2$, $C_3F_7OCFCF_2OCFCH=CH_2$
　　　　|　　　　|
　　　　$CF_3$　　$CF_3$ $CH_2=CHC_6F_{12}CH=CH_2$, $CH_2=CHCFOCF_2CF_2OCFCH=CH_2$,
　　　　　|　　　　　　　　|
　　　　　$CF_3$　　　　　$CF_3$ $CH_2=CHCF(OCF_2CF)_2OCF_2CF_2O(CFCF_2O)_3CFCH=CH_2$,
　　　　　　|　　　　|　　　　　　　　　|　　　　　|
　　　　　　$CF_3$　　$CF_3$　　　　　　$CF_3$　　$CF_3$ and $CH_2=CHCF(OCF_2CF_2)_3OCFCH=CH_2$.
　　　　　|　　　　　　　　　|
　　　　　$CF_3$　　　　　　　$CF_3$ 4. The method according to claim 1, wherein the powdered metallic zinc is used in an amount of from 20 to 5000 moles per mole of the iodine compound contained in the ethylene compound to be purified.

5. The method according to claim 1, wherein the aqueous acetic acid solution has an acetic acid concentration of from 0.5 to 99.0% by weight.

6. The method according to claim 1, wherein the aqueous acetic acid solution is used in an amount of from 0.5 to 3.0 moles, in terms of acetic acid, per mole of the powdered metallic zinc.

7. The method according to claim 1, wherein the reaction is carried out at a temperature ranging from 0° to 90° C.

* * * * *